(12) United States Patent
Hanefeld et al.

(10) Patent No.: US 7,462,750 B2
(45) Date of Patent: Dec. 9, 2008

(54) PARYLENE VARIANTS AND METHODS OF SYNTHESIS AND USE

(75) Inventors: Phillip Hanefeld, Mannheim (DE); Sven Horst, Reiskirchen (DE); Markus Meise, Berlin (DE); Michael Bognitzki, Marburg (DE); Andreas Greiner, Amoneburg (DE); Rakesh Kumar, Carmel, IN (US)

(73) Assignee: Specialty Coating Systems, Inc., Indianapolis, IN (US)

( * ) Notice: Subject to any disclaimer, the term of this patent is extended or adjusted under 35 U.S.C. 154(b) by 453 days.

(21) Appl. No.: 11/263,597

(22) Filed: Oct. 31, 2005

(65) Prior Publication Data

US 2007/0099019 A1   May 3, 2007

(51) Int. Cl.
  $C07C\ 22/00$   (2006.01)
  $C07C\ 19/08$   (2006.01)
(52) U.S. Cl. .................. 570/184; 570/127; 570/144
(58) Field of Classification Search .............. 570/127, 570/144, 184
See application file for complete search history.

(56) References Cited

U.S. PATENT DOCUMENTS

| | | | |
|---|---|---|---|
| 4,176,209 A | 11/1979 | Baker et al. | |
| 4,846,998 A | 7/1989 | Pohl et al. | |
| 4,886,923 A | 12/1989 | Ungarelli et al. | |
| 5,210,341 A | 5/1993 | Dolbier, Jr. et al. | |
| 5,284,933 A | 2/1994 | Dobeli, Jr. et al. | |
| 5,302,767 A | 4/1994 | Galley et al. | |
| 5,310,858 A | 5/1994 | Greiner et al. | |
| 5,536,892 A | 7/1996 | Dolbier, Jr. et al. | |
| 5,538,758 A | 7/1996 | Beach et al. | |
| 5,556,473 A | 9/1996 | Olson et al. | |
| 5,841,005 A | 11/1998 | Dolbier, Jr. et al. | |
| 5,849,962 A | 12/1998 | Dolbier, Jr. et al. | |
| 5,908,506 A | 6/1999 | Olson et al. | |
| 6,130,096 A | 10/2000 | Tinker et al. | |
| 6,150,499 A | 11/2000 | Dolbier, Jr. et al. | |
| 6,392,097 B1 | 5/2002 | Dolbier, Jr. et al. | |
| 6,646,150 B1 | 11/2003 | Sato et al. | |
| 6,869,698 B2 | 3/2005 | Chen et al. | |
| 2002/0026086 A1 | 2/2002 | Dolbier, Jr. et al. | |
| 2007/0148390 A1 | 6/2007 | Kumar | |
| 2007/0228606 A1 | 10/2007 | Hanefeld et al. | |

FOREIGN PATENT DOCUMENTS

JP   9025252   1/1997

OTHER PUBLICATIONS

Takayuki Shioiri et al., "Use of the aryl groups as the carboxyl synthon. Application to the synthesis of some natural products containing hydroxyl amino acid functions," *Pure & Appl. Chem.*, vol. 66, Nos. 10/11, pp. 2151-2154 (1994).

PCT/US 06/38012, International Search Report and the Written Opinion of the International Searching Authority, or the Declaration, dated Sep. 28, 2007.

*Primary Examiner*—Jafar Parsa
(74) *Attorney, Agent, or Firm*—Lowrie, Lando & Anastasi, LLP

(57) ABSTRACT

Fluorinated paracyclophane compounds represented by the formula

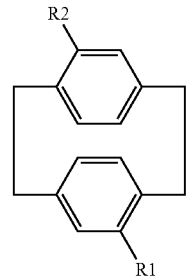

where least one of R1 and R2 comprises a fluorinated moiety is disclosed. These compounds can be utilized as precursor dimer compounds to produce polymeric coatings comprising copolymers of trifluorinated paraxylylene.

8 Claims, 5 Drawing Sheets

PARYLENE VARIANTS AND METHODS OF SYNTHESIS AND USE

BACKGROUND OF INVENTION

1. Field of Invention

This invention relates to paracyclophane precursors, synthesis thereof, and polymer formed therefrom and, in particular, to fluorinated paracyclophane dimers and synthesis and uses thereof.

2. Discussion of Related Art

Ungarelli et al., in U.S. Pat. No. 4,886,923, disclose a process for the preparation of tricycle 8,2,2,2 hexadeca 4,6, 10,12,13,15 hexane chlorinated in the benzene rings.

Galley et al., in U.S. Pat. No. 5,302,767, disclose [2,2] paracyclophane and derivatives thereof.

Dolbier, Jr. et al., in U.S. Pat. No. 5,841,005, disclose parylene AF4 synthesis and Beach et al., in U.S. Pat. No. 5,538,758, disclose a method and apparatus for the deposition of parylene AF4 onto semiconductor wafers.

SUMMARY OF THE INVENTION

One or more embodiments of the invention relate to aspects thereof pertinent to a coating of a copolymer of trifluoroethylene paraxylylene on a substrate.

One or more embodiments relate to aspects of the invention directed to paracyclophane comprising at least one trifluorinated moiety.

Further embodiments of the invention relate to aspects thereof pertinent to synthesizing a trifluorinated dimer. The method can comprise one or more acts of attaching at least one fluorinated carbonyl moiety on a paracyclophane and reducing the fluorinated carbonyl moiety to produce the trifluorinated dimer.

In accordance with one or more aspects, one or more embodiments of the invention relate to a method of synthesizing a polyfluorinated paracyclophane. The method can comprise one or more acts of heating a dibrominated paracyclophane and a fluorinated diene in the presence of a solvent and a mixture of palladium acetate, an amine, and an ether to produce a paracyclophane having at least one fluoro-diene pendent moiety; and hydrogenating the at least one fluoro-diene pendent moiety to produce the polyfluorinated paracyclophane.

In accordance with one or more embodiments, the invention is directed to a compound having the formula:

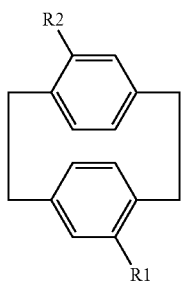

At least one of R1 and R2 comprises a fluorinated moiety.

One or more embodiments of the invention relate to aspects thereof pertinent to a substrate having the formula:

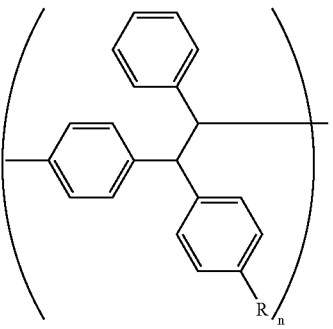

R is a moiety selected from the group consisting of a halogen, a sulfonyl, a carbonyl, a phenyl, an alcohol, and a diene and n is greater than 1.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DEFINITIONS

Figure 1A:
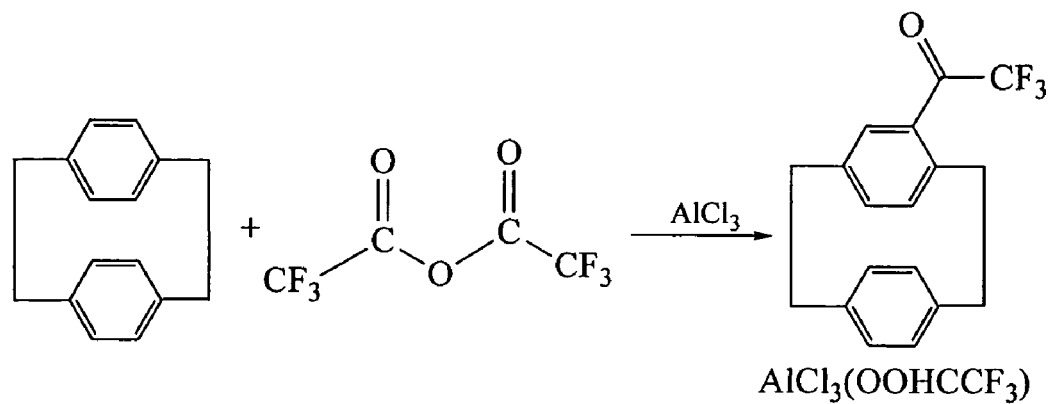
FIG. 1A illustrates a reaction scheme directed to the synthesis of an intermediate product for fluorinated paracyclophane in accordance with one or more embodiments of the invention.

As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. The term "PPX" refers to paraxylylene; "Ar" refers to an aryl group; "Ph" refers to a phenyl group; "Me" refers to a methyl group; and "DPX" refers to paracyclophane or di-para-xylylene.

DETAILED DESCRIPTION

This invention is not limited in its application to the details of construction and the arrangement of components set forth in the following description or illustrated in the drawings. The invention is capable of embodiments and of being practiced or of being carried out in various ways beyond those exemplarily presented herein.

The invention contemplates the modification of existing facilities to retrofit one or more systems, subsystems, or components and implement the techniques of the invention. Thus, for example, an existing facility including one or more installed systems can be modified to include one or more subsystems to perform in accordance with one or more embodiments exemplarily discussed herein including, for example, synthesize the compounds and/or polymers of the invention.

In accordance to one or more aspects, one or more embodiments of the invention are directed to patacyclophanes comprising at least one halogenated moiety. The paracyclophane can have one or more halogenated moieties pendent on a benzene ring thereof. In some cases, the halo-moiety is pendent on the paracyclophane only on a carbon of one or both benzene rings. The halogen moiety can comprise any halogen including, but not limited to fluorine. The halogen can be pendent on the benzene ring by a straight or branched moiety. Moreover, the straight or branched moiety can be saturated or have one or more double bonds. Where there are two or more pendent moieties, one or more moieties can be pendent on one or both rings of the paracyclophane compound. Indeed, in accordance with one or more embodiments of the invention, the halogenated paracyclophane can be represented by the formula:

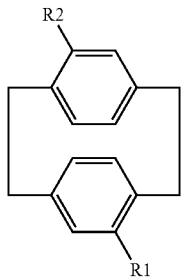

where at least one of R1 and R2 comprises a halogenated functional group, such as a fluorinated moiety. The other of R1 or R2 can also comprise a halogenated functional group such as a trifluorinated moiety or a moiety selected from the group consisting of an alkanet, alkene, alkyne, hydrogen, aromatic species, and other halogenated functionalities.

Some aspects of the invention further contemplate paracyclophane embodiments comprising one or more trifluorinated groups pendent on a ring carbon of the paracyclophane. Thus, in one or more particular embodiments of the invention, R1 and/or R2 can comprise any halogenated moiety including, but not limited to, trifluorinated-alkanes and/or alkenes such as, $-CF_3$, $-(CH_2)_nCF_3$, $-(CH_2)_x(CF_2)_nCF_3$, where n and $x \geqq 1$. Indeed, in accordance with one or more particular embodiments of the invention, R1 is $CF_3$ and R2 is hydrogen. Further embodiments of the invention can involve R1 as $-(CH_2)_x(CF_2)_nCF_3$ and R2 as $-(CH_2)_x(CF_2)_mCF_3$. In such embodiments, x, n, and/or m can be greater than or equal to one, but in some cases, n or m can also be zero. Particular embodiments, however, are directed to compounds where n and/or m equal five and x equals two. The pendent moieties, moreover, can accommodate one or more halogenated functionalities. Indeed, the halogenated moiety can comprise two or more types of halogen groups.

Other aspects of the invention also contemplate variations of the above-described embodiments. Thus, one or more aspects of the invention can be embodied as paracyclophanes consisting essentially of at least one halogenated moiety pendent on at least one ring of the paracyclophane and not on any of the ethano bridges, and in other aspects, as paracyclophanes comprising one or more fluorinated moieties pendent on the aromatic ring but may further include one or more halogenated species pendent on one or both ethano bridges.

The paracyclophane compounds of the invention can be synthesized by utilizing any suitable technique that provides the desired halogenated dimers. The synthesis process can involve a plurality of acts that provide desirably reactive intermediate compounds leading to the desired halogenated paracyclophane. In particular, synthesis reactions can involve any technique that can attach, or render pendent, any reactive functional group, on the paracyclophane. Further, any sequence of reaction paths can be utilized. Examples of suitable techniques that may be utilized to halogenated paracyclophane include, but are not limited to, epoxidation, esterification, cyclization, coupling, condensation, substitution, acylation, alkylation, halogenation, reduction, oxidation, rearrangement, dehydration, hydrogenation, and dehydrogenation reactions. One or more such techniques or intermediate acts can be performed in the presence of one or more catalysts. Further, one or more acts involved in the synthesis process can be performed in the presence of a solvent or carrier. The carrier can modify a physical property of one or reactive species but is preferably inert and recoverable. For example, the carrier can increase, or if desirable, decrease the activity of a reactant or even a catalyst in the one or more synthesis reactions. One or more carriers can be advantageously utilized to control the yield a desirable, or undesirable, reaction product or intermediate species, by, for example, facilitating formation of reactive radical species.

In accordance with one or more aspects directed to the synthesis of paraxylylene precursor species or dimers, the invention can comprise embodiments involving the reaction schematically illustrated in FIG. 1A. Synthesis of a fluorinated paracyclophane can comprise one or more acts of providing a paracyclophane compound and attaching one or more reactive functional groups on a ring carbon. Thus, as illustrated, attaching can involve rendering an anhydride functionality pendent on at least one ring carbon of the paracyclophane. The act of attaching can involve any suitable reactive technique and is not limited to a Friedel-Crafts acylation reaction as depicted in FIG. 1A. The exemplary acylation reaction can be facilitated by, for example, a Lewis acid, or one or more catalysts that can react or at least partially stabilize an intermediate complex. Other acylation techniques can be utilized to effect substitution, i.e., electrophilic aromatic substitution, between an arene and an acyl or an anhydride compound to provide an acylated product with a pendent halogenated carbonyl functional group.

The carbonylated paracyclophane can then be modified to a desired halogenated paracyclophane. For example, the fluorinated carbonyl functional group can be reduced to produce a paracyclophane having at least one trifluorinated pendent moiety as illustrated in the reduction reactions presented in FIG. 1B. The reduction can be effected in the presence of one or more solvents and/or one or more organic and/or inorganic acids. Indeed, any reactive technique that facilitates the deoxygenation of the pendent halogenated carbonyl group can be utilized. Such techniques can include, for example, Clemmenson or Wolff-Kishner reduction techniques. Other exemplary embodiments directed to reductive reactions can involve, for example, the enantioselective reduction with borane and catalytic oxazaborolidine.

The produced halogenated paracyclophane product can be purified utilizing any suitable technique including, but not limited to, drying, flash chromatography, extraction, distillation, recrystallization, and combinations thereof.

Further embodiments of the invention also contemplate other intermediate compounds along with other reactive techniques to produce the paracyclophane having one or more pendent halogenated moieties. The invention contemplates techniques or reactions such as, but not limited to, alkylation and Nencki reactive techniques, to attach one or more functional groups to the paracyclophane to produce a desired intermediate. For example, a nitro functional group pendent on a paracyclophane can be transformed to the pendent carbonyl group by converting the preformed nitronate salt in the presence of a strong acid. This may, in turn be reduced as described above. In some cases, permanganate facilitated oxidation may produce the desired pendent carbonyl functional group.

Figure 2A:
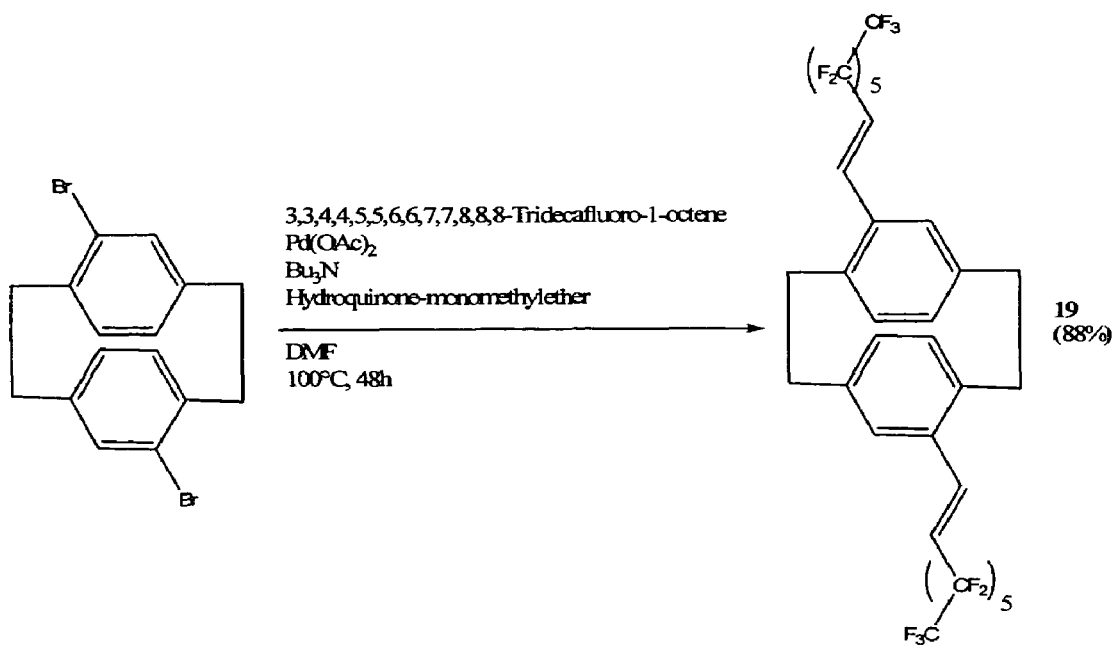
FIG. 2A illustrates a reaction scheme directed to the synthesis of an intermediate product for fluorinated paracyclophane in accordance with one or more embodiments of the invention.

Moreover, any suitable co-reactant with the paracyclophane may be utilized to produce the desired intermediate or halogenated product. For example, carbonylation techniques need not be limited to acylation but can, in some cases, involve benzoylation followed by a suitable substitution reaction to produce the halogenated carbonyl functional group pendent on paracyclophane. Indeed, in accordance with one or more aspects, one or more embodiments of the invention can utilize Heck reactive techniques to substitute one or more halogen functional groups pendent on the aromatic ring with a halogenated aryl, alkenyl, and/or benzyl group. As exemplarily illustrated in FIG. 2A, the reaction can involve platinum group metal catalysis coupling between an aryl halide with an alkenyl halide. The reaction presented in FIG. 2 illustrates a particular embodiment of the invention effected in the presence of, inter alia, a catalyst such as palladium diacetate, an amine such as tributylamine, and a solvent, such as dimethyl formamide. The coupling reaction can also utilize one or more organophoshine ligands such as tri-o-tolylphosphine. An ether, such as hydroquinone dimethyl ether can also be present in the coupling reaction.

In accordance with further aspects of the invention, one or more embodiments can comprise hydrogenation of the pendent halo-alkene moiety. Halogenation can be effected as according to the reaction exemplarily illustrated in FIG. 2B. Any suitable solvent and/or metal catalyst can be utilized to saturate the alkene linkage. For example, the solvent can be an alcohol such as, but not limited to, ethanol, and the catalyst can be a platinum group metal such as palladium.

Further aspects of the invention can be embodied as polymers comprising halogenated paraxylylenes. In accordance with one or more embodiments of the invention, the paraxylylene polymer can be made from one or more of the fluorinated paracyclophane compounds described herein. Thus, one or more aspects of the invention are directed to polymeric materials having one or more halogen moieties pendent on a ring thereof. One or more particular embodiments of the invention can be poly(trifluoro-paraxylylene), such as, but not limited to, poly(paraxylylene-co-trifluoroethylene paraxylylene) and poly(4-3,3,4,4,5,5,6,6,7,7,8,8-tridecafluorooctan paraxylylene) as represented below.

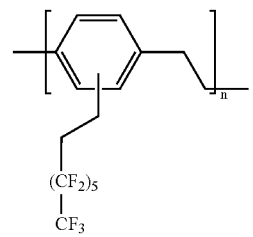

where n is greater than or equal to two.

Polymerization can be performed to provide a polymeric coating on a substrate surface. The substrate can be any desired article to be covered at any desired coating thickness. Thus, for example, the substrate can be an electronic device or even an medical device. In some cases, the article is intended to be utilized in an aggressive environment. For example, the article can be a sensor exposed to a corrosive fluid.

Coating of the substrate can be performed at any suitable temperature that effects, for example, vapor deposition polymerization of the precursor halogenated dimer compounds. In accordance with some embodiments of the invention, polymerization can be performed according to the Gorham method at a temperature greater than 500° C. at a vacuum. For example, polymerization can be performed at a pyrolization temperature of about 650° C. at a pressure of about $0.3 \times 10^{-2}$ bar. The deposition zone, or substrate, can be cooled to facilitate deposition, e.g., at a temperature of about 0° C.

The coatings of the invention can serve as protective, conformal and functional coatings on various substrates or components of electronic, medical, optoelectronic, and automotive assemblies or systems. The coatings can be present on all or at least a portion of a substrate surface. Examples include, but not limited to, about 0.1 to about 25 μm thick film on metals, ceramic, rubber and plastic substrates. Further examples include about 0.1 to 15 μm thick coatings on flexible PCB and other flexible medical devices or components thereof such as rubber, elastic and thin metals. Thus, one or more aspects of the invention involve at least one embodiment wherein a substrate has a coating that can extend, e.g., elongate, flex, or otherwise deform in conformation with the substrate, typically without delamination or separation. The polymeric materials may also be applied as an about 0.1 to 15 μm thick coating on electronic substrates and lenses. The invention, however, is not limited to a particular coating thickness and contemplates coatings having different thickness. Such embodiments may be advantageous where a coating can exhibit at least a partial sensitivity, e.g., permeability, under certain exposure conditions. Indeed, in accordance with certain embodiments of the invention, a substrate can have a plurality of types of coatings disposed on a surface thereof, each or any of which can have any desired thickness. Such configurations may provide advantageous features especially in embodiments when a portion of a substrate or device is intended to be exposed to a first environment and another portion is intended to be exposed to a second, different environment.

One or more aspects of the invention are further directed to derivatives produced by liquid coating techniques. Polymeric materials from these compounds can be produced by dissolving a precursor in a carrier, such as one or more solvents like, but not limited to, t-butyl acetate, toluene, methyl ethyl ketone, and acetone. The solution can then be applied accordingly by any suitable techniques including, for example, spray, dip, spin, brush, mist, curtain coater deposition.

The polymeric material can be a halogenated paraxylylene such as bromo-diphenyl paraxylylene as represented by the following formula.

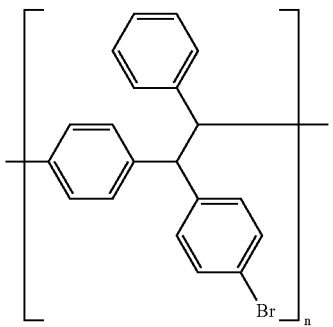

The polymeric material can have a glass transition temperature of about 248° C. The precursor of this polymeric material is typically soluble in DMF, dioxane, CHCl₃, THF, benzene, and toluene. The precursor can be synthesized by utilizing wet synthesis techniques with a paraxylylene derivative or variant.

In accordance with another embodiment of the invention, the polymeric material can be a sulfonated paraxylylene such as $SO_3H$-diphenyl paraxylylene as represented by the following formula.

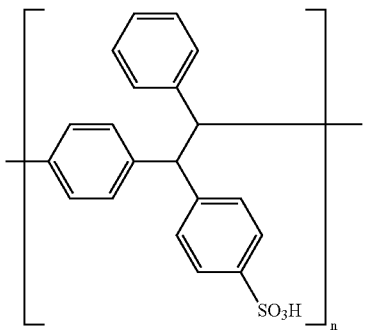

The polymeric material has a glass transition temperature of about 240° C. The precursor of this polymeric material is typically poorly soluble in dimethyl sulfoxide. The precursor can be synthesized by, for example, polymeranalogous reaction of a di-para-xylylene or a paraxylylene derivative or variant with $SO_3H$ (3%).

In accordance with another embodiment of the invention, the polymeric material can be a paraxylylene with a pendent alcohol such as diphenyl paraxylylene alcohol as represented by the following formula.

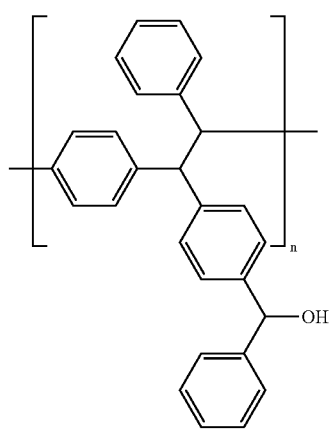

The polymeric material typically has a glass transition temperature of about 240° C. The precursor of this polymeric material is typically soluble in DMF, dioxane, CHCl₃, and THF. The precursor can be synthesized by a polymeranalogous reaction of a di-para-xylylene or a paraxylylene derivative or variant with CHOH-Ph (70%).

In accordance with another embodiment of the invention, the polymeric material can be diphenyl paraxylylene alcohol represented by the following formula.

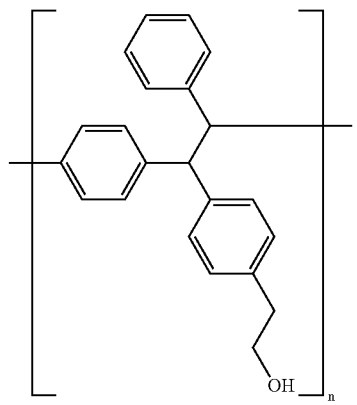

The polymeric material typically has a glass transition temperature of about 230° C. The precursor of this polymeric material is typically soluble in DMF, dioxane, CHCl₃, and THF. The precursor can be synthesized by, for example, a polymeranalogous reaction of a di-para-xylylene or a paraxylylene derivative or variant with CH$_2$CH$_2$OH (5%).

In accordance with another embodiment of the invention, the polymeric material can be diphenyl paraxylylene alcohol represented by the following formula.

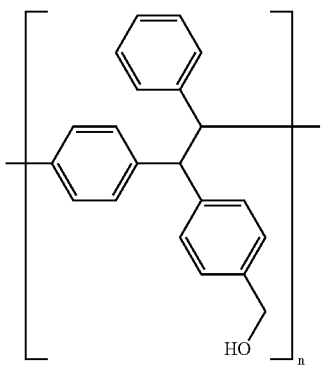

The polymeric material typically has a glass transition temperature of about 255° C. The precursor of this polymeric material is typically soluble in DMF, dioxane, and THF. The precursor can be synthesized by, for example, a polymeranalogous reaction of a di-para-xylylene or a paraxylylene derivative or variant with CH$_2$OH (50%).

In accordance with another embodiment of the invention, the polymeric material can be COOH diphenyl paraxylylene represented by the following formula.

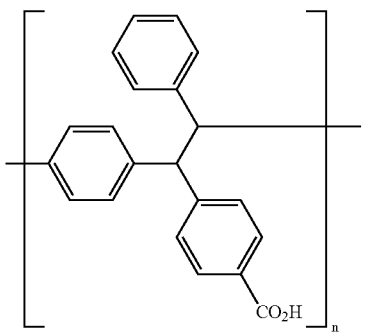

The polymeric material typically does not exhibit a glass transition temperature. The precursor of this polymeric material is typically soluble in methanol but not in water, aqueous KOH or ethanol. The precursor can be synthesized by, for example, a polymeranalogous reaction of a di-para-xylylene or a paraxylylene derivative or variant with COOH (60%).

In accordance with another embodiment of the invention, the polymeric material can be COOMe-diphenyl paraxylylene represented by the following formula.

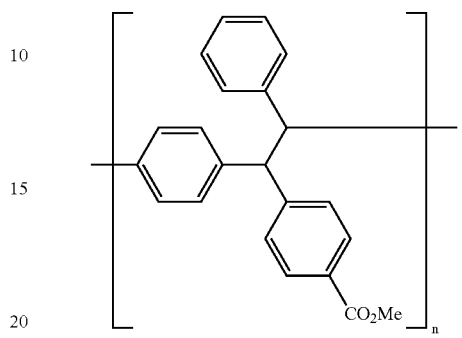

The polymeric material typically does not exhibit a glass transition temperature. The precursor of this polymeric material is typically soluble in methanol. The precursor can be synthesized by, for example, a polymeranalogous reaction of a di-para-xylylene or a paraxylylene derivative or variant with COOMe (60%).

In accordance with another embodiment of the invention, the polymeric material can be stilbene diphenyl paraxylylene represented by the following formula.

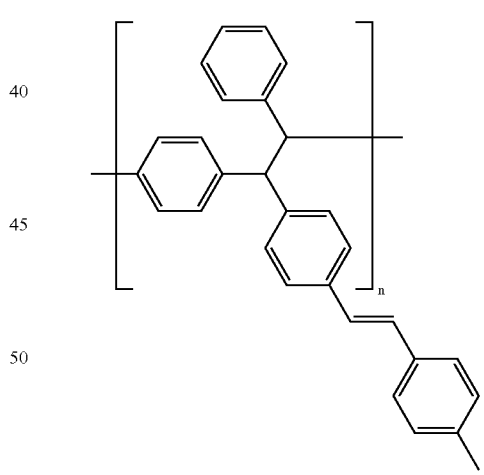

The polymeric material typically has a glass transition temperature of about 250° C. The precursor of this polymeric material is typically soluble in DMF, dioxane, CHCl$_3$, THF, and benzene. The precursor can be synthesized by, for example, a polymeranalogous reaction of a di-para-xylylene or a paraxylylene derivative or variant with CH═CHAr.

In accordance with another embodiment of the invention, the polymeric material can be stilbene diphenyl paraxylylene represented by the following formula.

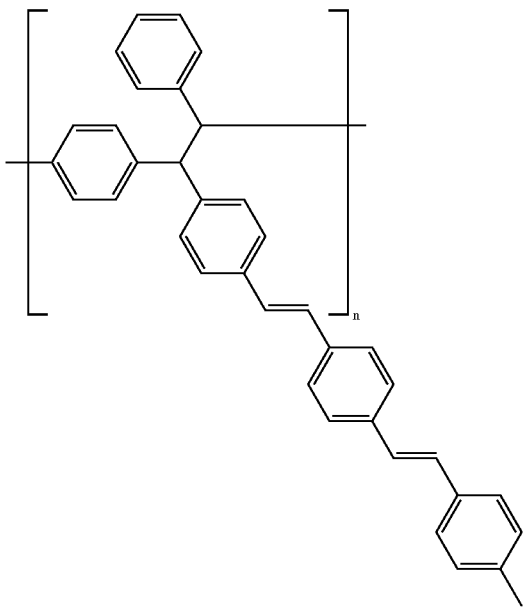

The polymeric material can have a glass transition temperature of about 250° C. The precursor of this polymeric material is typically soluble in DMF, dioxane, CHCl$_3$, THF, and benzene. The precursor can be synthesized by, for example, a polymeranalogous reaction of a di-para-xylylene or a paraxylylene derivative or variant with CH=CHAr.

EXAMPLES

The function and advantages of these and other embodiments of the invention can be further understood from the examples below, which illustrate the benefits and/or advantages of the one or more systems and techniques of the invention but do not exemplify the full scope of the invention.

Example 1

Synthesis of trifluoroethyl-[2,2]paracyclophane (trifluoroethyl-DPX)

In this example, trifluorinated paracyclophane was synthesized in two reaction steps.

Trifluoroacedic acid anhydride (TFAA) was distilled over P$_2$O$_5$ to ensure full reactivity. The solvent, dichloromethane (DCM), was dried over CaH$_2$. In a 3 L round flask, with an attached reflux condenser assembly, about 81 g of AlCl$_3$ and about 85 mL of TFAA were dissolved in about 1.4 L of DCM, a under protective atmosphere of argon. The assembly was cooled with ice. About 50 g of paracyclophane (DPX) was slowly added to the mixture. A foaming exothermic reaction was observed. The colour of the mixture changed from colourless to deep red-brown. After stirring for about 1 h and subsequent warming to room temperature, the mixture was refluxed at a temperature of about 40° C. for about three hours.

The mixture was slowly quenched the next day with about 200 mL of concentrated HCl. The organic phase was separated from the aqueous phase. The former was washed with water and the DCM was used to extract all organic residues from the aqueous phase. All organic phases were dried with MgSO$_4$. After the solvent was removed, a dark brown solid crude product was obtained.

The crude intermediate product was purified by recrystallization in hexane and methanol. The total yield was about 44.5 g of intermediate product (62.5%).

The Friedel-Crafts acylation reaction is illustrated in FIG. 1A. The intermediate product, acylated paracyclophane was characterized as presented in Table 1.

TABLE 1

| Characteristics of acylated paracyclophane. | |
|---|---|
| $^1$H-NMR (300 MHz, CDCl$_3$) | δ=6.79-6.55(m, 7H, Ar—H), 3.39-3.04(m, 8H, Ar—CH$_2$—CH$_2$—Ar)ppm |
| GC-MS | 100% M=304, product |
| FT-IR | ν=2927s(—C—H val), 2894s(—C—H val), 2857s(—C—H val), 1708s(—C=O), 1593s(—C=C arom), 1500s(—C=C arom), 1437s(—C=C arom), 1204s(—C—F), 1136s(—C—F), 844(—C—H def)cm$^{-1}$ |

In a 250 mL round bottom flask, with an attached reflux condenser and under a protective atmosphere, about 1.5 g of iodine and about 15.2 mL of hypophosphoric acid were refluxed in about 72 mL of acedic acid (solvent). About 5 g of the intermediate product synthesized above were dissolved in about 28 mL of acedic acid. The solution was slowly added to the boiling mixture. The reaction was refluxed for about six days. GC-MS samples were retrieved every day to monitor the progress of the reaction.

The mechanism of the reaction is believed to proceed according to the following reactions.

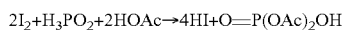

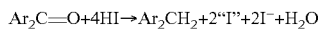

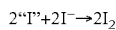

and resulting an overall reaction scheme according to the following.

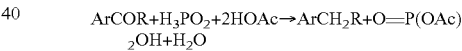

After about six days, the solution was quenched with pure water. Ether was used as an extracting solvent. The organic phase was dried with MgSO$_4$ over night. After solvent removal, the crude product was obtained as a white solid.

The crude product was purified by flash chromatography in a silica column with hexane as solvent to remove remaining by-products (alcohol). The product was recrystallized from hexane to obtain a white crystalline powder.

Figure 1B:
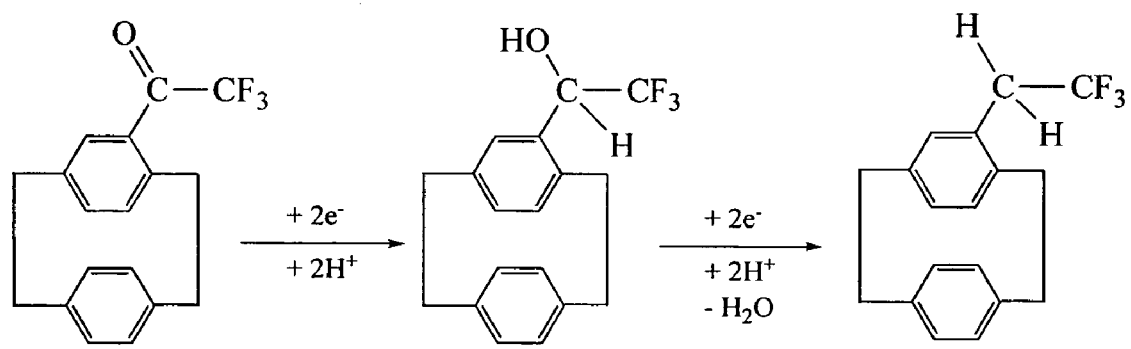
FIG. 1B illustrates a reaction scheme directed to the synthesis of a fluorinated paracyclophane in accordance with one or more embodiments of the invention.

The overall reaction is illustrated in FIG. 1B. The product was characterized as shown in Table 2.

TABLE 2

| Characteristics of trifluorinated paracyclophane. | |
|---|---|
| $^1$H-NMR (200 MHz, CDCl$_3$) | δ=6.83-6.32(m, 7H, Ar—H), 3.40-3.30(m, 2H, CH$_2$—CF$_3$), 3.12-2.86(m, 8H, Ar—CH$_2$—CH$_2$—Ar), 2.7-1.2 ppm |
| GC-MS | Before chromatography: 24.65% M=306, alcohol(2-hydroxy-trifluoro-ethyl-DPX) 75.25% M=288, product(trifluoroethyl-DPX) After chromatography: 100% M=288, product |
| FT-IR | ν=2953s(—C—H val), 2924s(—C—H val), 2851s(—C—H val), 1594s(—C=C arom), 1493s(—C=C arom), 1416s(—C=C arom), |

TABLE 2-continued

Characteristics of trifluorinated paracyclophane.

1354s(—C—F), 1254(—C—F),
1113(—C—F), 797(—C—H def)in cm$^{-1}$

Example 2

Synthesis of poly(paraxylylene-co-trifluoroethylene paraxylylene)

Figure 3:
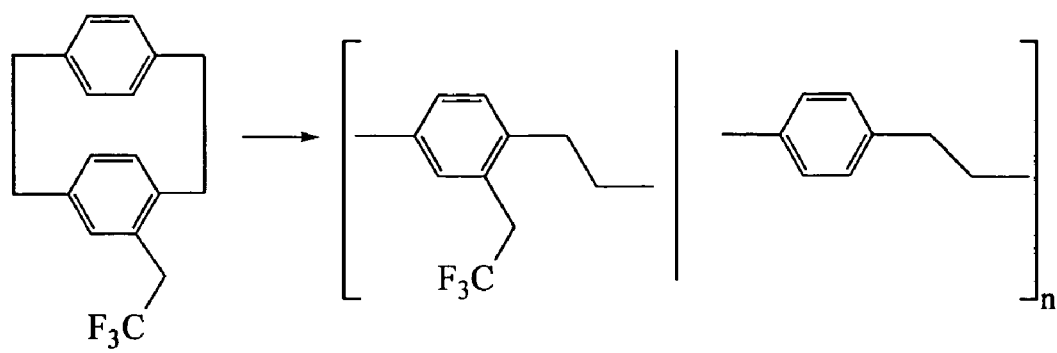
FIG. 3 illustrates a reaction scheme directed to the production of a fluorinated paraxylylene in accordance with one or more embodiments of the invention.

Vapor phase deposition and condensation polymerization, as schematically illustrated in FIG. 3, produced a coating of poly(paraxylylene-co-trifluoroethylene paraxylylene) (parylene-coTFE or PPX-coTFE). The parylene-coTFE formed an insoluble film having a measured contact angle, against water, of about 105-degree. Thus, the polymeric coating exhibited high water repellence and self-cleaning behavior.

A DSC analysis was performed from 25° to 300° C. at a heating rate of about 10 K per minute. A weak glass transition was found at about 120° C. A strong endothermic process, which could be interpreted as a second glass transition or melting point, was observed at about 210° C.

A TGA-IR analysis was performed from 25° to 800° C. at a heating rate of about 10 K per minute in a nitrogen atmosphere. An about 5 wt % decrease at about 435° C. was observed. A mean decomposition temperature of about 494° C. was also noted. The residual ash was composed of approximately 18% of the total weight of the original polymer sample. Moreover, IR analysis of the resultant gases indicated the presence of aromatic bonds as well aliphatic groups. $CF_3^-$ signals were observed at about the decomposition temperature.

Figure 4:
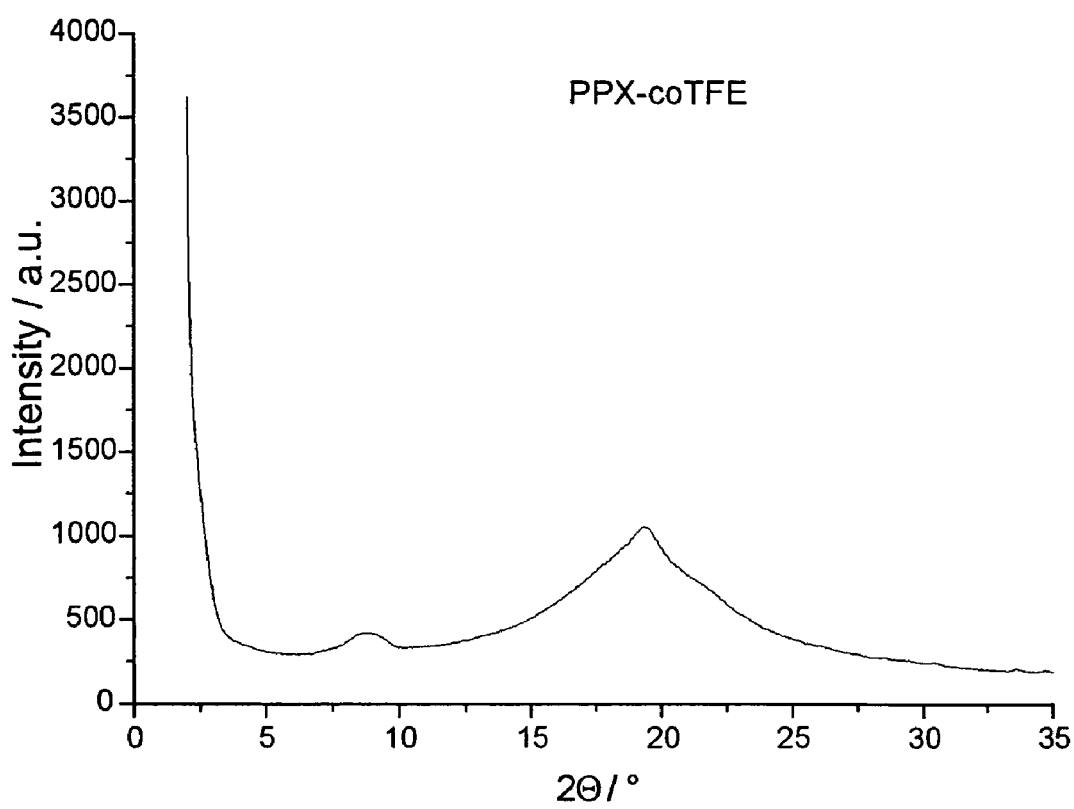
FIG. 4 is a reproduction of a wide angle x-ray scattering profile of a fluorinated paraxylylene produced in accordance with one or more embodiments of the invention.

Wide angle X-ray scattering analysis (WAXS), reproduced in FIG. 4, showed that the polymer had amorphous and crystalline habits. The crystalline habit did not indicate any sharp peaks although a strong halogen peak was noted. Known peaks corresponding to paraxylylene (alpha and beta varieties) were not observed.

Mechanical properties analyses of the polymeric coating, at a thickness of about 10 μm, were performed according to ISO 527 and DIN 53504 procedures (at about 1 mm/min at about 23° C.). The polymeric material showed weaker Young's modulus relative to known parylene coatings (PPX-N and PPX-C) as shown in Table 3, below.

TABLE 3

Comparative Modulus
of poly(paraxylylene-co-trifluoroethyleneparaxylylene)

| Test | PPX-N | PPX-C | PPX-coTFE |
|---|---|---|---|
| E Modulus (MPa) | 2093 | 2552 | 1906 |

Several films were prepared by vapor phase polymerization, from the precursor dimer produced as substantially described in Example 1, at various temperatures. The polymeric films were transparent and about 2-3 μm thick. ATR-IR spectroscopic mapping showed no quantitative difference in intensity for the characteristic bonds which shows that no there was no substantial difference in polymeric composition.

Contact angles against water were also observed to be about 105° (±1). The higher contact angle relative to parylene-HT is believed to be a consequence of the presence of the flexible fluorine functionalities and to the relatively higher fluorine concentration.

Example 3

Synthesis of 4,16-Di-(3,3,4,4,5,5,6,6,7,7,8,8,8-tridecafluoro-1-octene)-[2,2]paracyclophane A Heck coupling reaction was performed as illustrated in FIG. 2A to produce an intermediate paracyclophane having a pendent fluoro-alkene. A 250 ml reactor was charged under argon atmosphere with a solvent, N,N-Dimethyl-formamide (DMF). The educts as listed in Table 4 were also charged into the reactor.

TABLE 4

Reactants

| Educts | Formula | M [g/mol] | Equiv. | Mole [mmol] | Mass [g] |
|---|---|---|---|---|---|
| 4,16-Dibromo[2,2]paracyclophane | $C_{16}H_{14}Br_2$ | 366.0 | 1.0 | 5.78 | 2.12 |
| 3,3,4,4,5,5,6,6,7,7,8,8,8-tridecafluoro-1-octene | $C_8H_3F_{13}$ | 346.09 | 5.0 | 28.9 | 10.0 |
| Hydroquinone dimetyl ether | $C_7H_8O_2$ | 124.14 | — | — | 0.5 |
| Tributylamine | $C_9H_{27}N$ | 185.35 | | 71.22 | 13.2 |
| Palladium(II) diacetate | $C_4H_6O_4Pd$ | 224.49 | Cat. | 0.11 | 0.0247 |
| Tri-o-tolylphosphine | $C_6H_{14}$ | 304.36 | | 1.0 | 0.0944 |
| N,N-Dimethyl-formamide | $C_4H_9ON$ | | | | 100 ml |

After heating and stirring for about forty-eight hours at a temperature of about 100° C., the mixture a precipitate as produce about adding an about 2% aqueous HCl. The crude product was filtered and recrystallized twice using ethanol. The yield of the intermediate product was about 88%. This intermediate product had an observed melting point of about 93° C. The observed characteristics of the intermediate product are listed in Table 5.

Figure 2B:
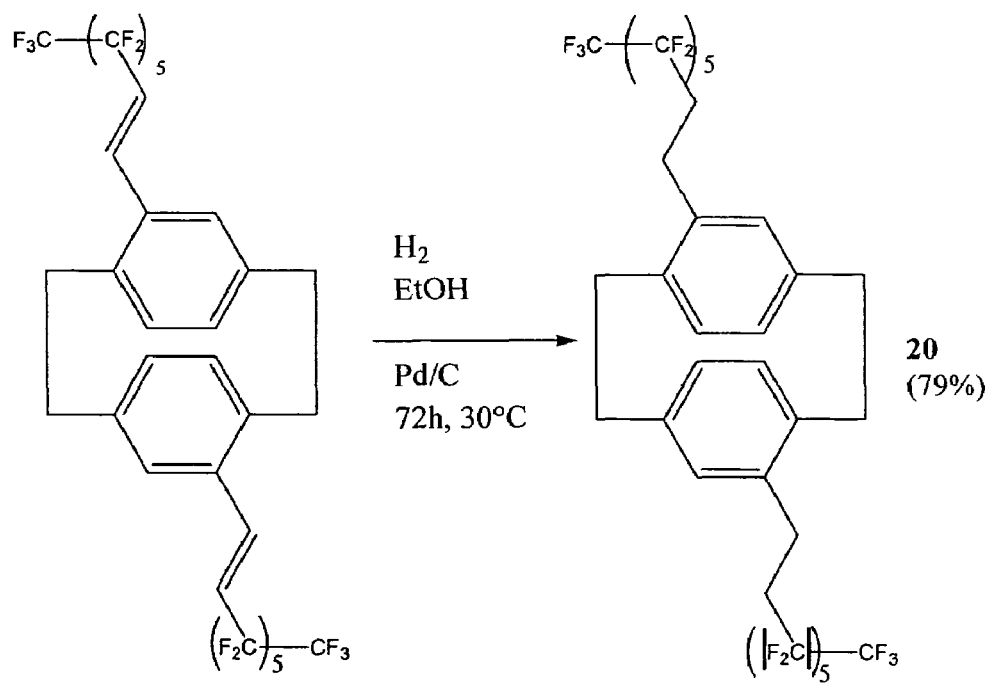
FIG. 2B illustrates a reaction scheme directed to the synthesis of a fluorinated paracyclophane in accordance with one or more embodiments of the invention.

The intermediate product was hydrogenated according to the reaction shown in FIG. 2B by introducing the educts listed in Table 6 in a 100 mL flask. A hydrogen atmosphere was used as a blanket over the mixture during stirring at about 40° C. for about seventy-two hours.

The reaction yield was determined to be about 79%. The product was observed to have a melting point of about 64° C. Characteristics of the product are listed in Table 7, below.

TABLE 5

Characteristics by spectroscopical and elemental analysis of tridecafluoro-1-octene paracyclophane.

| | |
|---|---|
| $^1$H-NMR (300 MHz, CDCl$_3$) | δ/ppm: 6.41(s, 4H, CH=CH), 5.69-5.89(m, 6H, CH$_{ar}$), 3.00(s, 8H, CH$_2$) |
| $^{13}$C-NMR (300 MHz, CDCl$_3$) | δ/ppm: 139.59(C$_{ar}$), 132.98(C$_{ar}$), 125.65(C$_{ar}$), 125.52(C$_{ar}$), 125.39(C$_{ar}$), 125.36(C$_{ar}$), 12503(C=C), 124.36(C=C), 35.61(CH$_2$) |
| $^{19}$F-NMR (200 MHz, CDCl$_3$) | −81.16(t, J=11, CF$_3$), −111.03(m, CF$_2$), −122(m, CF$_2$), −126(m, CF$_2$) |
| FT-IR | ν/cm$^{-1}$: 802(Fingerprint Ar), 833(Fingerprint Ar), 1192(C—F), 1230(C—F), 1465(C=C), 2930(C—H$_{al}$), 3030(C—H$_{ar}$) |
| Elemental analysis | C$_{32}$H$_{18}$F$_{26}$ M=896.44 g/mol Cal..: 42.87%(C)2.02%(H)55.11%(F) Fou.: 44.81%(C)3.72%(H)51.47%(F) |

TABLE 6

Reactants

| Educts | Formula | M [g/mol] | Equiv. | Mole [mmol] | Mass [g] |
|---|---|---|---|---|---|
| Intermediate Product | C$_{32}$H$_{18}$F$_{26}$ | 552.09 | 1.0 | 51.8 | 1.0 |
| Hydrogen | H$_2$ | | 2.0 | — | — |
| Pd/C | — | — | — | — | 0.15 |
| Ethanol (solvent) | C$_2$H$_6$O | 46.0 | — | — | 20 ml |

TABLE 7

Characteristics by spectroscopical and elemental analysis of tridecafluorooctane paracyclophane.

| | |
|---|---|
| $^1$H-NMR (300 MHz, CDCl$_3$) | δ/ppm: 6.41(s, 4H, CH=CH), 3.00(s, 8H, CH$_2$)1.36(s, 4H, CH$_2$), 1.19(m, 4H, CH$_2$) |
| $^{13}$C-NMR (300 MHz, CDCl$_3$) | δ/ppm: 138.58(C$_{ar}$), 132.01(C$_{ar}$), 124.50(C$_{ar}$), 45.58(CH$_2$), 34.69(CH$_2$), 29.33(CH$_2$), 26.70(CH$_2$) |
| $^{19}$F-NMR (200 MHz, CDCl$_3$) | −81.16(t, J=11, CF$_3$), −111.03(m, CF$_2$), −122(m, CF$_2$), −126(m, CF$_2$) |
| FT-IR | ν/cm$^{-1}$: 802(Fingerprint Ar), 833(Fingerprint Ar), 1192(C—F), 1230(C—F), 1465(C=C), 2930(C—H$_{al}$), 3030(C—H$_{ar}$) |
| Elemental analysis | C$_{32}$H$_{22}$F$_{26}$ M=900, 13 g/mol Calc.: 42.68%(C)2.46%(H)54.86%(F) Fou.: 44.73%(C)3.38%(H)51.89%(F) |

Example 4

Synthesis of poly(4-3,3,4,4,5,5,6,6,7,7,8,8,8-tridecafluorooctane paraxylylene)

A pyrolysis oven was used for the vapor deposition polymerization (Gorham method) to produce the polymer, poly(4-3,3,4,4,5,5,6,6,7,7,8,8,8-tridecafluorooctane paraxylylene). About 0.5 g of the precursor synthesized as substantially described in Example 3 was pyrolyzed at a temperature of about 650° C. at a pressure of about $0.3 \times 10^{-2}$ mbar. The deposition zone was cooled to a temperature of about 0° C. Films of the polymer were collected on glass or stainless steel plates.

The polymer is observed to be insoluble in standard organic chloroform, tetrahydrofuran (THF), and toluene. The characteristics of the polymeric coating are listed in Table 8, below.

TABLE 8

Characteristics of polytridecafluorooctane paraxylylene.

| | |
|---|---|
| FT-IR | ν/cm$^{-1}$: 3046(m, sp$^2$), 2921(m, sp$^3$), 2856(m, sp$^3$), 1605/1540/1453/1205, (w, C—F), 950-826(Fingerprint Ar) |
| Differential Scanning Calorimetry | No glass transition was detected but a recrystallization exotherm at 200° C. about 5% weight loss under nitrogen atmosphere was detected by thermogravimetrical analysis at about 231° C. |
| Contact angle (static) against water | about 120° |
| Elongation at break | about 400% |

Example 5

Synthesis of Liquid-Polymerized Paraxylylene Variants

Paracyclophane variants were synthesized by Gilch-type polymerization in solution. Notably, the precursor compounds could be also utilized in vapor phase polymerization techniques but HCl may be generated as by-product.

Table 9, below lists representative liquid-polymerizable paraxylylene precursor materials along with some physical properties thereof.

TABLE 9

Liquid based paraxylylene variants.

| Name | Chemical Structure | Synthesis route | Properties |
|---|---|---|---|
| Poly(α-(4-bromophenyl)-α'-phenyl-p-xylylene) | [structure] | Gilch | Tg: 248° C. Soluble in: DMF, Dioxane, CHCl$_3$, THF, Benzol, Toluol |
| Poly(α-(3-methylphenyl)-α'-phenyl-p-xylylene) | [structure] | Gilch | Tg: 202° C. Soluble in: DMF, Dioxane, CHCl$_3$, THF, Benzol, Toluol |
| Poly(α,α'-diphenyl-p-xylylene) | [structure] | Gilch | Tg: 175° C. Soluble in: DMF, Dioxane, CHCl$_3$, THF, Benzol, Toluol |

Figure 5:
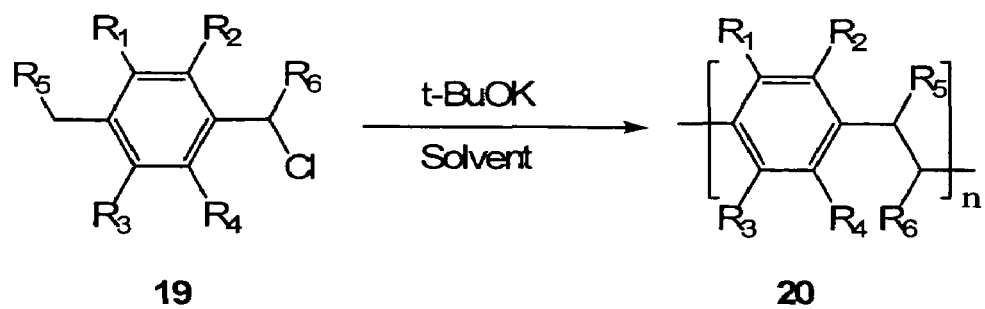
FIG. 5 illustrates a reaction scheme directed to liquid-based paraxylylene precursor synthesis in accordance with one or more embodiments of the invention.

The Gilch-type polymerization reaction scheme is typically illustrated in FIG. 5. Chloromethylated toluene derivatives 19 were used as precursors for the preparation of new PPXs by base-induced Gilch-type polymerization. Strong bases such as potassium tert-butanolate (t-BuOK) were used as bases. However, other initiating species may also be utilized.

$R_1$, $R_2$, $R_3$, $R_4$, $R_5$, $R_6$ can be any functional group such as, but not limited to, hydrogen, an alkyl, alkanet, an aryl, an alcohol, or combinations thereof.

Polymerization reactions were performed in organic solvents like tetrahydrofuran, toluene, dioxane, with at least a twofold molar excess of base related to the precursors 19. Polymerizations were performed at a temperature of between about −50° C. up to about +150° C., with reactions time from a few minutes up to several hours. Some selected detailed examples are provided below.

Molecular weights were determined by gel permeation chromatography versus polystyrene standards, with chloroform as the eluent at a temperature of about 20° C. Glass transition temperatures were analyzed by differential scanning calorimetry, at a heating rate of about 10 K/min.

Example 6

Synthesis of poly(α-(4-bromophenyl)-α'-phenyl-paraxylylene)

Figure 6:
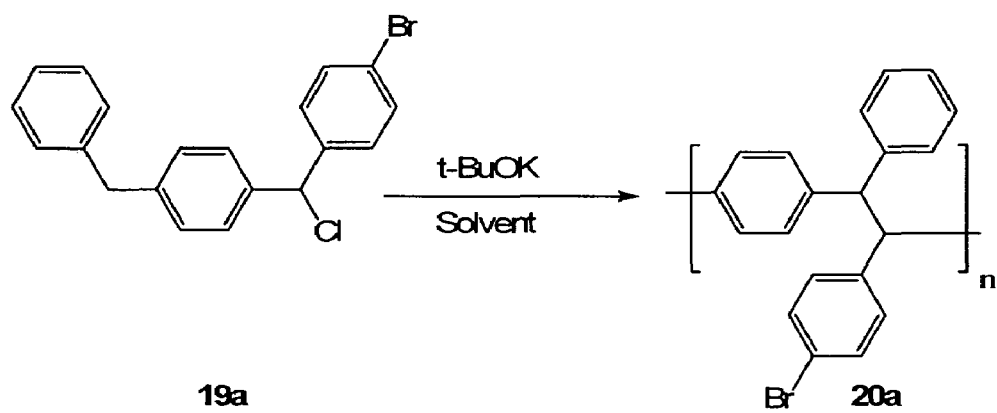
FIG. 6 illustrates another reaction scheme directed to another liquid-based paraxylylene precursor synthesis in accordance with one or more embodiments of the invention.

The synthesis reaction is illustrated in FIG. 6.

A flame-dried flask equipped with a dropping funnel, magnetic stirring bar, and a reflux condenser was charged under argon atmosphere with exclusion of moisture by about 1.82 g (about 16.2 mmol) of t-BuOK in about 85 mL dry THF. The mixture was heated to reflux with quick stirring and quickly charged by use of the dropping funnel with about 8.1 mmol of the precursor 19a, dissolved in about 12 ml of dioxane. The mixture was heated for about three hours to reflux. The hot mixture was poured in a ten fold volume excess of cold methanol. The precipitated polymer 20a was isolated, reprecipitated from a mixture of chloroform and methanol and finally dried in vacuum at a temperature of about 50° C. The yield was about 75% of the product 20a, with $M_w$=263,000; $Mn_n$=117,000; $M_w/M_n$=2.2.

Example 7

Synthesis of poly(α-(3-methylphenyl)-α'-phenyl-p-xylylene)

Figure 7:
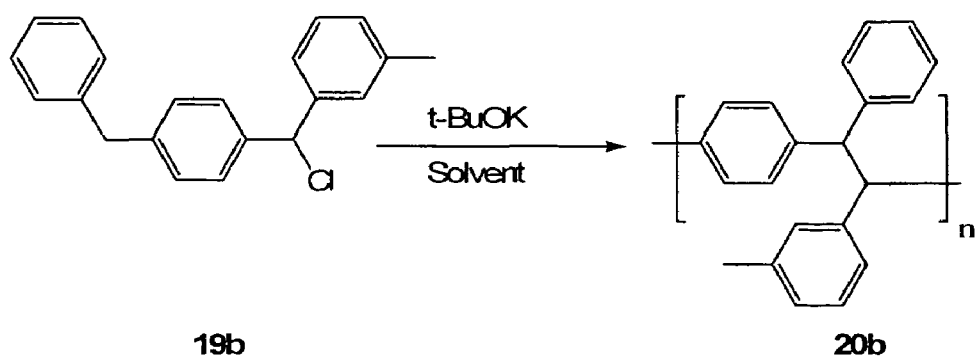
FIG. 7 illustrates another reaction scheme directed to another liquid-based paraxylylene precursor synthesis in accordance with one or more embodiments of the invention.

The synthesis reaction is illustrated in FIG. 7.

A flame-dried flask equipped with a dropping funnel, magnetic stirring bar, and a reflux condenser was charged under argon atmosphere with exclusion of moisture by about 1.82 g (about 16.2 mmol) of t-BuOK in about 85 ml dry THF. The mixture was heated to reflux with quick stirring and quickly charged by use of the dropping funnel with 8.1 mmol of precursor 19b dissolved in 12 ml of dioxane. The mixture was heated for about hours to reflux. The hot mixture was poured in ten fold volume excess of cold methanol. The precipitated polymer 20b was isolated, reprecipitated from chloroform/methanol and finally dried in vacuum at about 50° C. The yield of product 20b was determined to be about 70% with $M_w$=317,000; $M_n$=132,000; and $M_w/M_n$=2.4.

Example 8

Synthesis of poly(α,α'-diphenyl-p-xylylene)

Figure 8:
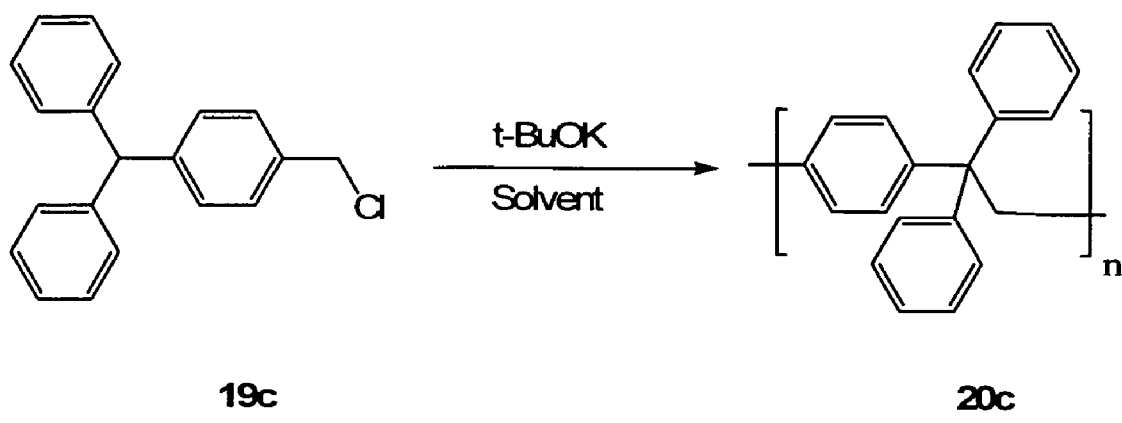
FIG. 8 illustrates another reaction scheme directed to another liquid-based paraxylylene precursor synthesis in accordance with one or more embodiments of the invention.

The synthesis reaction is illustrated in FIG. 8.

A flame-dried flask equipped with a dropping funnel, magnetic stirring bar, and a reflux condenser was charged under argon atmosphere with exclusion of moisture by about 1.82 g (about 16.2 mmol) of t-BuOK in about 85 ml dry THF. The mixture was heated to reflux with quick stirring and quickly charged by use of the dropping funnel with about 8.1 mmol of precursor 19c, dissolved in about 12 ml of dioxane. The mixture was heated for 3 hours to reflux. The hot mixture was poured in ten fold volume excess of cold methanol. The precipitated polymer 20c was isolated, reprecipitated from chloroform/methanol and finally dried in vacuum at about 50° C. The yield of product 20c was about 62% with $M_w$=49,000; $M_n$=39,000; $M_w/M_n$=1.3.

Having now described some illustrative embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Thus, the invention is not limited to a particular halogen and can be practical with any halogenated functional group or moiety that exhibits a halogenated behavior.

Further, acts, elements, and features discussed only in connection with one embodiment are not intended to be excluded from a similar role in other embodiments.

It is to be appreciated that various alterations, modifications, and improvements can readily occur to those skilled in the art and that such alterations, modifications, and improvements are intended to be part of the disclosure and within the spirit and scope of the invention.

Moreover, it should also be appreciated that the invention is directed to each feature, system, subsystem, or technique described herein and any combination of two or more features, systems, subsystems, or techniques described herein and any combination of two or more features, systems, subsystems, and/or methods, if such features, systems, subsystems, and techniques are not mutually inconsistent, is considered to be within the scope of the invention as embodied in the claims.

Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is therefore to be understood that the embodiments described herein are presented by way of example only and that, within the scope of the appended claims and equivalents thereto; the invention may be practiced otherwise than as specifically described.

What is claimed is:

1. A compound having the formula:

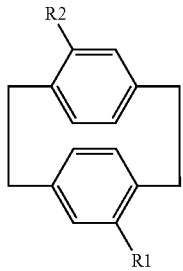

wherein at least one of R1 and R2 comprises at least one of a trifluoroalkane and a trifluoroalkene.

2. The compound of claim 1, wherein R1 is $CF_3$.

3. The compound of claim 2, wherein R2 is hydrogen.

4. The compound of claim 1, wherein R1 is $CH_2CH_2(CF_2)_nCF_3$ and $1 \leq n$.

5. The compound of claim 4, wherein n=5.

6. The compound of claim 5, wherein R2 is $CH_2CH_2(CF_2)_mCF_3$ and $1 \leq m$.

7. The compound of claim 6, wherein m=5.

8. A paracyclophane comprising at least one trifluoroethylene moiety.

* * * * *